United States Patent [19]

Parris

[11] Patent Number: 5,004,636
[45] Date of Patent: Apr. 2, 1991

[54] ROLL-TYPE TOILET TISSUE HAVING HEMORRHOID-TREATING MEDICATION THEREIN

[76] Inventor: Michael Parris, 39 Wilder Rd., Monsey, N.Y. 10952

[21] Appl. No.: 382,212

[22] Filed: Jul. 20, 1989

[51] Int. Cl.[5] .............................................. B32B 5/16
[52] U.S. Cl. .................................. 428/43; 428/537.5; 428/906; 252/91; 514/882; 424/445
[58] Field of Search ...................... 428/43, 537.5, 906; 252/91; 424/445; 514/882

[56] References Cited

U.S. PATENT DOCUMENTS

| | | |
|---|---|---|
| 1,775,998 | 9/1930 | Greenberg . |
| 2,389,736 | 11/1945 | Muise . |
| 3,138,533 | 6/1964 | Helm . |
| 4,426,418 | 1/1984 | Coleman . |
| 4,508,728 | 4/1985 | Nagai et al. ............................ 514/184 |
| 4,657,691 | 4/1987 | Hara et al. .............................. 252/91 |

Primary Examiner—Alexander S. Thomas
Attorney, Agent, or Firm—Terry M. Gernstein

[57] ABSTRACT

A roll-type toilet tissue is formed of three layers, with one layer being formed by a hemorrhoid-treating medication and being sandwiched between two other layers.

1 Claim, 3 Drawing Sheets

ROLL-TYPE TOILET TISSUE HAVING HEMORRHOID-TREATING MEDICATION THEREIN

TECHNICAL FIELD OF THE INVENTION

The present invention relates to the general art of paper products, and to the particular field of toilet tissue.

BACKGROUND OF THE INVENTION

There are numerous people who suffer from hemorrhoids. This affliction can range from mild cases having mild discomfort associated therewith to extreme cases requiring surgical intervention.

Hemorrhoids can be extremely painful, and thus, there have been several medications proposed for treating such problem. These medications are often in the form of creams and ointments which are often odious to apply. Therefore, such forms of medication have not achieved full acceptance in the market.

Some medication has been provided in applicator pad form, but such pads are often small and inconvenient to use. Furthermore, because of their construction, these medicated pads are not amenable to a plurality of uses.

Accordingly, there is a need for a means of applying hemorrhoid medication in a simple expedient manner and which means is amenable to more than the single use of applying such medication.

OBJECTS OF THE INVENTION

It is a main object of the invention to provide a means of applying hemorrhoid medication in a simple expedient manner.

It is another object of the invention to provide a means of applying hemorrhoid medication in a simple expedient manner which means is amenable to more than the single use of applying such medication.

SUMMARY OF THE INVENTION

These, and other, objects are achieved by placing hemorrhoid medication on roll form toilet tissue.

In this manner, the medicated product is in a form which is familiar to all people. This will encourage people to use the product, and can serve a dual purpose of applying the medication as well as the usual clean-up function associated with toilet tissue.

The convenience, ease of use and multiple functions of the product will encourage its use by those who would otherwise hesitate, or refuse, to use cream-type products or pad-type products.

DETAILED DESCRIPTION OF THE PREFERRED EMBODIMENT OF THE INVENTION

Figure 1:
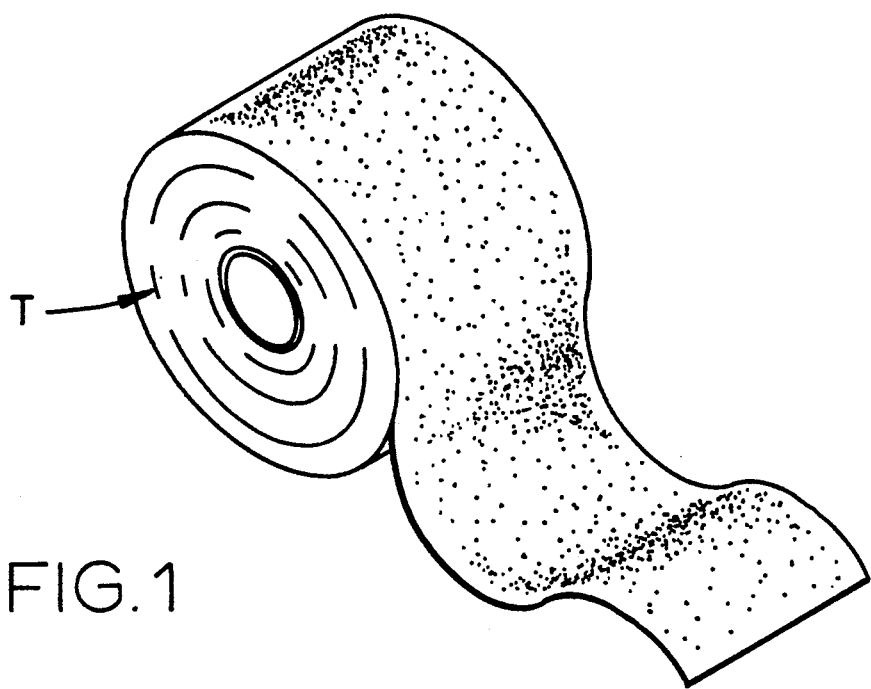
FIG. 1 is a perspective view of a roll of medicated toilet tissue of the present invention.
Figure 2:
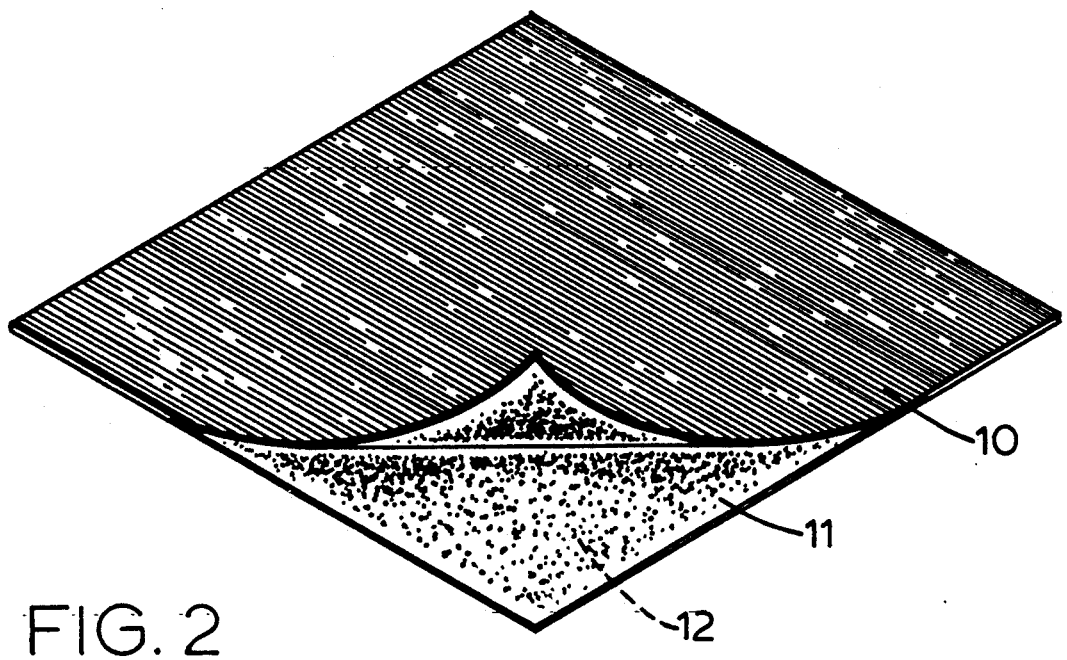
FIG. 2 is a perspective view of a medication-impregnated toilet tissue embodying the present invention in which the paper sheets have been pulled apart to illustrate the layer of medication on the inside surfaces of the sheets.
Figure 3:
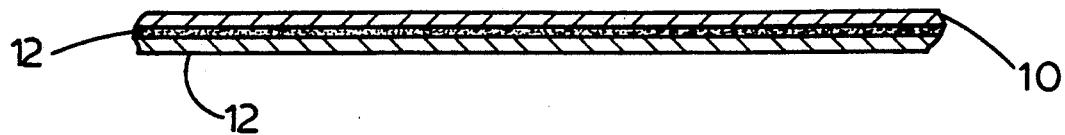
FIG. 3 is cross section of the sheet shown in FIG. 2.

As shown in the accompanying drawing figures, the medicated roll-type toilet tissue T of the present invention is a roll of multi-layer product which comprises a sheet of paper 10 and another sheet of paper 11 between which there is placed a layer of hemorrhoid medication 12. This medication can be a cream type medication, or a powder form or the like. In order to illustrate this, in FIG. 2, the sheet 10 has one corner pulled up as though the layer of medication 12 between the sheets would divide. In practice, however, the sheets could not usually be so separated without tearing the sheets, for the layer of medication 12 acts as a binder to hold the sheets 10 and 11 as a laminated pile.

Figure 4:
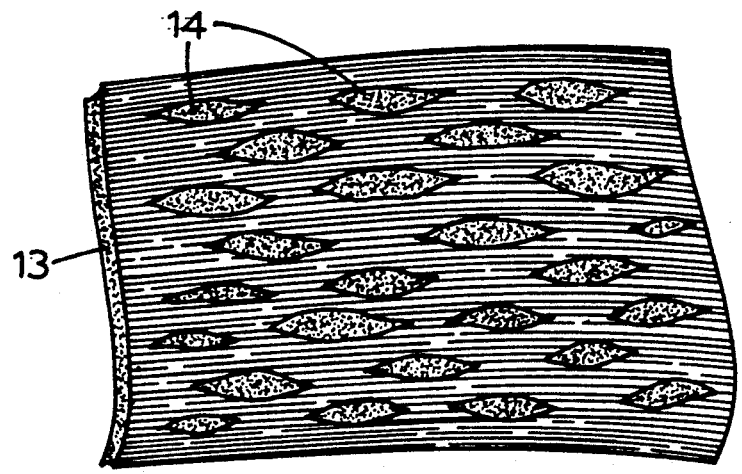
FIG. 4 is a greatly magnified view of a section of the sheet in which the holes or pores are formed in the making of the sheet, showing the pores and the medication lying therein.

The sheets 10 and 11 may be made of facial tissue which as illustrated in FIG. 4 has a multiplicity of relatively large openings or pores 14. The fibers of the sheet are very loosely held together, since the sheet is practically unsized. This fact, coupled with the presence of the pores 14, permits the sheet to rapidly break up or disintegrate, in the presence of water, into relatively small fibers which readily flow down the drain with the flush water.

Figure 5:
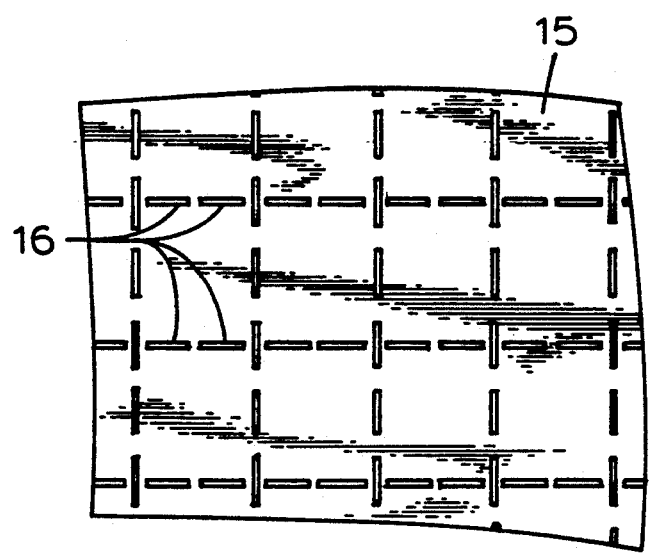
FIG. 5 is a greatly magnified view of the sheet in which the pores or openings are produced by cross-perforating the sheet.

As shown in FIG. 5, a less porous sheet 15 may be used if desired, but in such case, it is preferable to provide the sheet with perforations 16 which may crisscross each other so as to divide the sheet into a large number of small sections which readily disintegrate when wet. In making the medicated sheets of the present invention, the sheets 10 and 11 may begin as parts of continuous strips 10a and 11a, preferably in roll form, and from the rolls the strips are brought together and passed through rollers 17. In the trough 18 formed by converging strips, a quantity of hemorrhoid-treating medication 19, either in liquid form or in plastic form, accumulates, the medication being allowed to flow into the tough from a supply pipe 20 and drip nozzles 21. In the preferred form of the invention, the medication includes a mixture of alcohol and powder and can be in slurry form, but can be other forms of hemorrhoid-treating medication without departing from the scope of the present invention. The rollers 17 are so spaced that only a predetermined amount of medication is allowed to remain between the strips as the strips advance. The quantity remaining may be increased or decreased by separating or bringing together the rollers 17.

Figure 6:
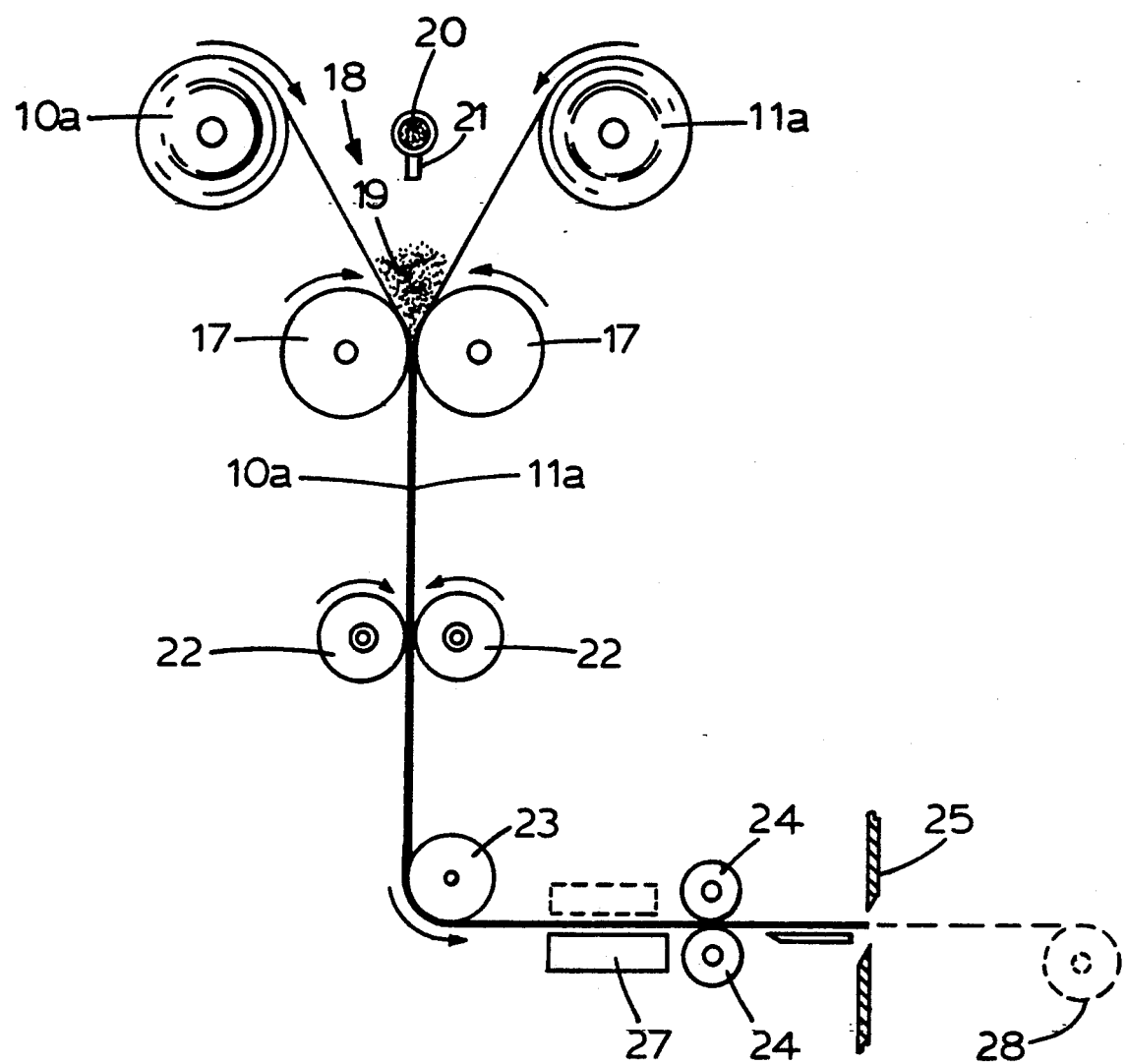
FIG. 6 is a schematic view showing the apparatus for making the medication containing roll-type toilet tissue of the present invention.

The strips 10a and 11a are held together by the adhesive and binding action of the medication, and in this condition may be passed over or between heating rollers 22 so as to partially dry the medication. The laminated sheet may then pass over a guide roller 23 and between feed rollers 24 to a cutoff knife 25. The strip is stored and dispensed in roll form and is thus perforated in sheet lengths by perforating mechanism 27 diagrammatically illustrated in dotted lines in FIG. 6 and then wound onto a spool 28, and then cut off as the proper length of roll is achieved.

In passing between the rollers 17, some of the medication is squeezed into the pores 14 or the perforations 16 depending upon whether the strip has natural or artificially formed openings and thus interlocks with the strips and aids in holding the strips together as a laminated pile.

Besides serving this purpose, the openings or pores in the sheets in use permit the medication to escape from between the sheets onto the proper areas to be medicated.

Since the openings or pores 14 in the sheet 13 are irregular in shape and are located at random, when two such sheets are superposed the openings for the most part do not register in the two sheets. This aids in strengthening the sheet for its intended use.

It is understood that while certain forms of the present invention have been illustrated and described herein, it is not to be limited to the specific forms or arrangements of parts described and shown.

I claim:
1. A roll of toilet tissue product comprising:
   at least three layers;
   one layer being sandwiched between the other two layers;
   said one layer being formed of hemorrhoid treating medication including alcohol and powder; and
   the other two layers comprising paper and having a porosity selected to permit said hemorrhoid-treating medication to flow therethrough for application by contact with the area to be treated.

* * * * *